US012659741B2

(12) United States Patent
Paul et al.

(10) Patent No.: US 12,659,741 B2
(45) Date of Patent: Jun. 16, 2026

(54) PROXIMITY-BASED DATA ACCESS AUTHENTICATION AND AUTHORIZATION IN AN ANALYTE MONITORING SYSTEM

(71) Applicant: Dexcom, Inc., San Diego, CA (US)

(72) Inventors: Nathanael Richard Paul, Knoxville, TN (US); Jorge R. Barreras, Dania Beach, FL (US)

(73) Assignee: Dexcom, Inc., San Diego, CA (US)

( * ) Notice: Subject to any disclaimer, the term of this patent is extended or adjusted under 35 U.S.C. 154(b) by 481 days.

(21) Appl. No.: 18/047,250

(22) Filed: Oct. 17, 2022

(65) Prior Publication Data

US 2023/0126810 A1 Apr. 27, 2023

Related U.S. Application Data

(60) Provisional application No. 63/262,959, filed on Oct. 22, 2021.

(51) Int. Cl.
| | |
|---|---|
| *G16H 10/60* | (2018.01) |
| *A61B 5/00* | (2006.01) |
| *H04W 12/065* | (2021.01) |
| *A61B 5/145* | (2006.01) |

(52) U.S. Cl.
CPC ......... *H04W 12/065* (2021.01); *A61B 5/0004* (2013.01); *A61B 5/002* (2013.01); *G16H 10/60* (2018.01); *A61B 5/14532* (2013.01); *A61B 2560/0209* (2013.01); *A61B 2562/08* (2013.01)

(58) Field of Classification Search
CPC ... A61B 5/0004; A61B 5/002; A61B 5/14532; A61B 2560/0209; A61B 2562/08; H04W 12/065; H04W 12/06; G16H 10/60; G16H 10/65

USPC .......................................................... 705/2, 3
See application file for complete search history.

(56) References Cited

U.S. PATENT DOCUMENTS

| | | | | |
|---|---|---|---|---|
| 2018/0182491 | A1* | 6/2018 | Belliveau | G16H 20/17 |
| 2018/0338726 | A1* | 11/2018 | Yarger | G16Z 99/00 |
| 2019/0036688 | A1* | 1/2019 | Wasily | H04L 9/3231 |
| 2019/0173885 | A1* | 6/2019 | Kamath | H04W 12/06 |
| 2019/0190913 | A1* | 6/2019 | Love | A61B 5/1451 |

(Continued)

OTHER PUBLICATIONS

International Search Report and Written Opinion for Application No. PCT/US2022/078241, mailed Feb. 1, 2023, 14 pages.

*Primary Examiner* — Alaaeldin M. Elshaer
(74) *Attorney, Agent, or Firm* — Klarquist Sparkman, LLP

(57) ABSTRACT

Methods and apparatus are provided for securely obtaining access to patient data associated with a patient using a sensor system configured for monitoring analyte levels of a patient. In one aspect, a method includes receiving, at a display device, one or more communications from the sensor system, wherein the one or more communications include identifiable information associated with the sensor system and are transmitted by the sensor system via an advertisement channel; inserting, at the display device, the identifiable information in a web request; providing, at the display device, the web request including the identifiable information to a data management system to request access to the patient data; and obtaining access to the patient data through a web browser upon the data management system verifying that the identifiable information matches a second identifiable information stored in the patient data.

17 Claims, 4 Drawing Sheets

(56)        References Cited

U.S. PATENT DOCUMENTS

| | | | |
|---|---|---|---|
| 2019/0214147 A1* | 7/2019 | Ariely | G16H 10/40 |
| 2020/0036792 A1 | 1/2020 | Palin et al. | |
| 2020/0259823 A1 | 8/2020 | Biehl et al. | |
| 2022/0409052 A1* | 12/2022 | Taub | G16H 40/67 |

* cited by examiner

300

PROXIMITY-BASED DATA ACCESS AUTHENTICATION AND AUTHORIZATION IN AN ANALYTE MONITORING SYSTEM

CROSS REFERENCE TO RELATED APPLICATIONS

This application claims priority to and benefit of U.S. Provisional Patent Application No. 63/262,959, filed Oct. 22, 2021, which is hereby assigned to the assignee hereof and hereby expressly incorporated by reference in its entirety as if fully set forth below and for all applicable purposes.

BACKGROUND

Field

The present application relates generally to medical devices such as analyte sensors, and more particularly to systems, devices, and methods related to securely providing access to patient data (including analyte data generated by an analyte sensor).

Description of the Related Technology

Granting or providing secure access to patient data remains challenging. As a result, there is a need for improved systems and method to enable patient data (e.g., including medical device data, such as analyte data), to be securely accessed by a patient or a physician, while decreasing burdens on stakeholders.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method of securely obtaining access to patient data associated with a patient using a sensor system for monitoring analyte levels of the patient. The method also includes receiving, at a display device, one or more communications from the sensor system, wherein the one or more communications include identifiable information associated with the sensor system and are transmitted by the sensor system via an advertisement channel; inserting, at the display device, the identifiable information in a web request; providing, at the display device, the web request including the identifiable information to a data management system to request access to the patient data; and obtaining access to the patient data through a web browser upon the data management system verifying that the identifiable information matches a second identifiable information stored in the patient data. Other embodiments of this aspect include corresponding computer systems, apparatus, and computer programs recorded on one or more computer storage devices, each configured to perform the actions of the methods.

In some embodiments, the sensor system is a continuous analyte sensor system, each of the one or more communications is configured to describe an analyte value of a host to the display device, and the identifiable information may include a defined number of latest analyte values reported by the continuous analyte sensor system, the sensor system is a continuous sensor system that is configured to continuously transmit communications to the display device, the one or more communications may include a defined number of latest communications transmitted by the continuous sensor system, and the identifiable information may include received signal strength indicator values for the defined number of latest communications. Implementations of the described techniques may include hardware, a method or process, or computer software on a computer-accessible medium.

In some embodiments, the one or more communications are transmitted via a low range wireless communication network, the sensor system is configured to communicate via the low range wireless communication network using a Bluetooth low energy (BLE) chip, and the identifiable information may include chip identifier data associated with the BLUE chip. Implementations of the described techniques may include hardware, a method or process, or computer software on a computer-accessible medium.

In some embodiments, the low range wireless communication network is associated with a communication protocol, and the communication protocol is associated with a set of data channels and a set of advertisement channels may include the advertisement channel that is used to transmit the one or more communications. Implementations of the described techniques may include hardware, a method or process, or computer software on a computer-accessible medium.

In some embodiments, the web request may include one or more authentication token fields that are maintained by the display device, and access to the patient data through the web browser is obtained upon the data management system verifying that the identifiable information matches the second identifiable information stored in the patient data and the one or more authentication token fields match one or more second authentication token fields maintained by the data management system. Implementations of the described techniques may include hardware, a method or process, or computer software on a computer-accessible medium.

Another general aspect includes a method of authorizing access to patient data associated with a patient using a sensor system for monitoring analyte levels of the patient. The method includes receiving, at a data management system, a web request from a display device, the web request indicating a request for access to the patient data and including identifiable information associated with the sensor system, wherein the identifiable information is provided by one or more communications that are transmitted to the display device from the sensor system via an advertisement channel; verifying, at a data management system, that the identifiable information matches a second identifiable information stored in the patient data; and granting, at a data management system, the request for access to the patient data based on the verifying. Other embodiments of this aspect include corresponding computer systems, apparatus, and computer programs recorded on one or more computer storage devices, each configured to perform the actions of the methods.

In some embodiments, the sensor system is a continuous analyte sensor system, each of the one or more communications is configured to describe an analyte value of a host to the display device, and the identifiable information may include a defined number of latest analyte values reported by the continuous analyte sensor system, the sensor system is a continuous sensor system that is configured to continuously transmit communications to the display device, the one or more communications may include a defined number of latest communications transmitted by the continuous sensor system, and the identifiable information may include received signal strength indicator values for the defined number of latest communications. Implementations of the described techniques may include hardware, a method or process, or computer software on a computer-accessible medium.

In some embodiments, the one or more communications are transmitted via a low range wireless communication network, the sensor system is configured to communicate via the low range wireless communication network using a Bluetooth low energy (BLE) chip, and the identifiable information may include chip identifier data associated with the BLUE chip. Implementations of the described techniques may include hardware, a method or process, or computer software on a computer-accessible medium.

In some embodiments, the low range wireless communication network is associated with a communication protocol, and the communication protocol is associated with a set of data channels and a set of advertisement channels may include the advertisement channel that is used to transmit the one or more communications. Implementations of the described techniques may include hardware, a method or process, or computer software on a computer-accessible medium.

In some embodiments, the web request may include one or more authentication token fields that are maintained by the display device, and access to the patient data through the web browser is obtained upon the data management system verifying that the identifiable information matches the second identifiable information stored in the patient data and the one or more authentication token fields match one or more second authentication token fields maintained by the data management system. Implementations of the described techniques may include hardware, a method or process, or computer software on a computer-accessible medium.

DETAILED DESCRIPTION

Currently, most medical device systems perform authentication and authorization with passwords or one-time codes.

For example, if a stakeholder, such as a physician, wants access to a patient's medical data (e.g., analyte data), a patient must upload this data to a cloud data platform. Then, the physician will log in to a portal associated with the cloud platform and proceed to download the patient's previously uploaded data.

However, for the cloud data platform to allow the physician to download the patient's previously uploaded data, the cloud data platform must be able to identify the physician as being authorized by the patient to access the data (e.g., the physician and the patient information must be tied). For example, in certain cases, the patient may have access to a mobile application that communicates with the cloud data platform, in which case, the physician may ask the patient to find a one-time code that is generated by the mobile app and sent to the cloud data platform. After receiving the one-time code that is generated by the mobile app, the physician will input the code into the portal associated with the cloud data platform to prove that the physician has been authorized by the patient to access the data. The cloud data platform then compares the code provided by the physician and the code transmitted by the mobile app to the cloud data platform. If the two codes are the same, the cloud data platform provides the physician with access to the patient's data.

Further, for many existing medical data systems, once authorization of a certain user is established and access is granted, the user gets read access to all medical data (i.e., gets an all or nothing read access). Accordingly, existing medical data systems are not configured to enforce finer grained permissions.

Therefore, how patients and stakeholders interact with medical data can be wholly transformed. Today's systems are antiquated. If the security and usability of these systems are improved, stakeholders will find the improved systems equally if not more useful, while the burden to use these systems is decreased.

Accordingly, certain embodiments described herein involve the use of proximity (e.g., physical distance and/or wireless communication range) to make authentication and authorization highly usable and less burdensome. The use of proximity in authentication and authorization is advantageous because if an attacker is not in range of a patient's on-body device radio signal (e.g., transmitter Bluetooth Low Energy (BLE)), then the attacker will not be able to hear or intercept data from that signal (e.g., transmitter BLE antenna signal). In rare cases, some attackers may be equipped with more advanced equipment to extend the listening range for a BLE signal. However, if a stakeholder is willing to accept the minimal risk associated with close-proximity attacker devices, then the stakeholder can gain a high degree of usability in their health management system.

Figure 1A:
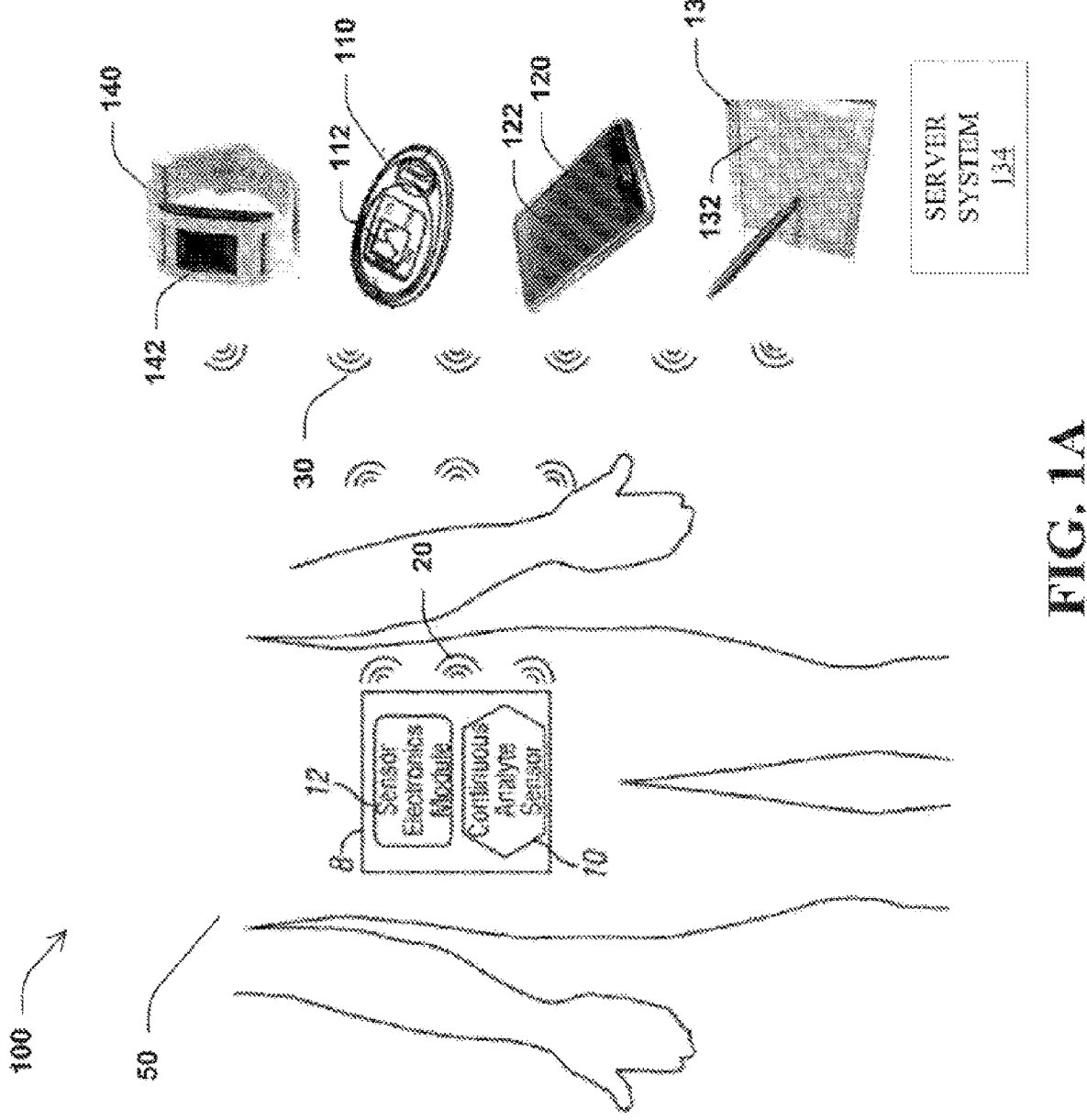
FIG. 1A illustrates an example diabetes management system, according to some embodiments disclosed herein.

FIG. 1A depicts a disease management system 100 ("system 100"), such as a diabetes management system, that may be used in connection with embodiments of the present disclosure that involve gathering, monitoring, and/or providing information regarding analyte values present in a user's body, including for example the user's blood glucose values. System 100 depicts aspects of analyte sensor system 8 (hereinafter "SS 8") that may be communicatively coupled to display devices 110, 120, 130, and 140, and/or server system 134.

In some embodiments, SS 8 is provided for measurement of an analyte in a host or a user. By way of an overview and an example, SS 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices, such as display devices 110, 120, 130, 140, and/or server system 134. Paragraphs [0137]-[0140] and FIGS. 3A, 3B, and 4 of U.S. App. No. 2019/0336053 further describe an on-skin sensor assembly that, in certain embodiments, may be used in connection with SS 8. Paragraphs [0137]-[0140] and FIGS. 3A, 3B, and 4 of U.S. App. No. 2019/0336053 are incorporated herein by reference.

In certain embodiments, SS 8 includes an analyte sensor electronics module 12 and an analyte sensor 10 associated with analyte sensor electronics module 12. In certain embodiments, analyte sensor electronics module 12 includes electronic circuitry associated with measuring and processing analyte sensor data or information, including algorithms associated with processing and/or calibration of the analyte sensor data/information. Analyte sensor electronics module 12 may be physically/mechanically connected to analyte sensor 10 and can be integral with (i.e., non-releasably attached to) or releasably attachable to analyte sensor 10.

Analyte sensor electronics module 12 may also be electrically coupled to analyte sensor 10, such that the components may be electromechanically coupled to one another (e.g., (a) prior to insertion into a patient's body, or (b) during the insertion into the patient's body). Analyte sensor electronics module 12 may include hardware, firmware, and/or software that enable measurement and/or estimation of levels of the analyte in a host/user via analyte sensor 10 (e.g., which may be/include a glucose sensor). For example, analyte sensor electronics module 12 can include one or more potentiostats, a power source for providing power to analyte sensor 10, other components useful for signal processing and data storage, and a telemetry module for transmitting data from the sensor electronics module to one or more display devices. Electronics can be affixed to a printed circuit board (PCB) within SS 8, or platform or the like, and can take a variety of forms. For example, the electronics can take the form of an integrated circuit (IC), such as an Application-Specific Integrated Circuit (ASIC), a microcontroller, a processor, and/or a state machine.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Analyte sensor 10 is configured to measure a concentration or level of the analyte in the host. The term analyte is further defined by paragraph [0117] of U.S. App. No. 2019/0336053. Paragraph [0117] of U.S. App. No. 2019/0336053 is incorporated herein by reference. In some embodiments, analyte sensor 10 comprises a continuous glucose sensor, such as a subcutaneous, transdermal (e.g., transcutaneous), or intravascular device. In some embodiments, analyte sensor 10 can analyze a plurality of intermittent blood samples. Analyte sensor 10 can use any method of glucose-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs

[0072]-[0076] of U.S. application Ser. No. 13/827,577. Paragraphs [0072]-[0076] of U.S. application Ser. No. 13/827,577 are incorporated herein by reference.

With further reference to FIG. 1A, display devices 110, 120, 130, and/or 140 can be configured for displaying displayable sensor information that may be transmitted by sensor electronics module 12 (e.g., in a customized data package that is transmitted to the display devices based on their respective preferences). Each of display devices 110, 120, 130, or 140 may respectively include a display such as touchscreen display 112, 122, 132, and/or 142 for displaying sensor information and/or analyte data to a user and/or receiving inputs from the user. For example, a graphical user interface (GUI) may be presented to the user for such purposes. In certain embodiments, the display devices may include other types of user interfaces such as voice user interface instead of or in addition to a touchscreen display for communicating sensor information to the user of the display device and/or receiving user inputs. In certain embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1A may include a custom or proprietary display device, for example, analyte display device 110, especially designed for displaying certain types of displayable sensor information associated with analyte data received from sensor electronics module 12 (e.g., a numerical value and/or an arrow, in certain embodiments). In certain embodiments, one of the plurality of display devices 110, 120, 130, 140 includes a smartphone, such as mobile phone 120, based on an Android, iOS, or another operating system configured to display a graphical representation of the continuous sensor data (e.g., including current and/or historic data). In certain embodiments, disease management system 100 further includes a medical delivery device (e.g., an insulin pump or pen). Sensor electronics module 12 may be configured to transmit sensor information and/or analyte data to medical delivery device. The medical delivery device (not shown) may be configured to administer a certain dosage of insulin or another medicament to the user based on the sensor information and/or analyte data (e.g., which may include a recommended insulin dosage) received from the sensor electronics module 12.

Server system 134 may be used to directly or indirectly collect analyte data from SS 8 and/or the plurality of display devices, for example, to perform analytics thereon, generate universal or individualized models for glucose levels and profiles, provide services or feedback, including from individuals or systems remotely monitoring the analyte data, perform or assist SS 8 and display device 150 with identification, authentication, etc., according to the embodiments described herein, so on. Note that, in certain embodiments, server system 134 may be representative of multiple systems or computing devices that perform the functions of server system 134 (e.g., in a distributed manner).

Figure 1B:
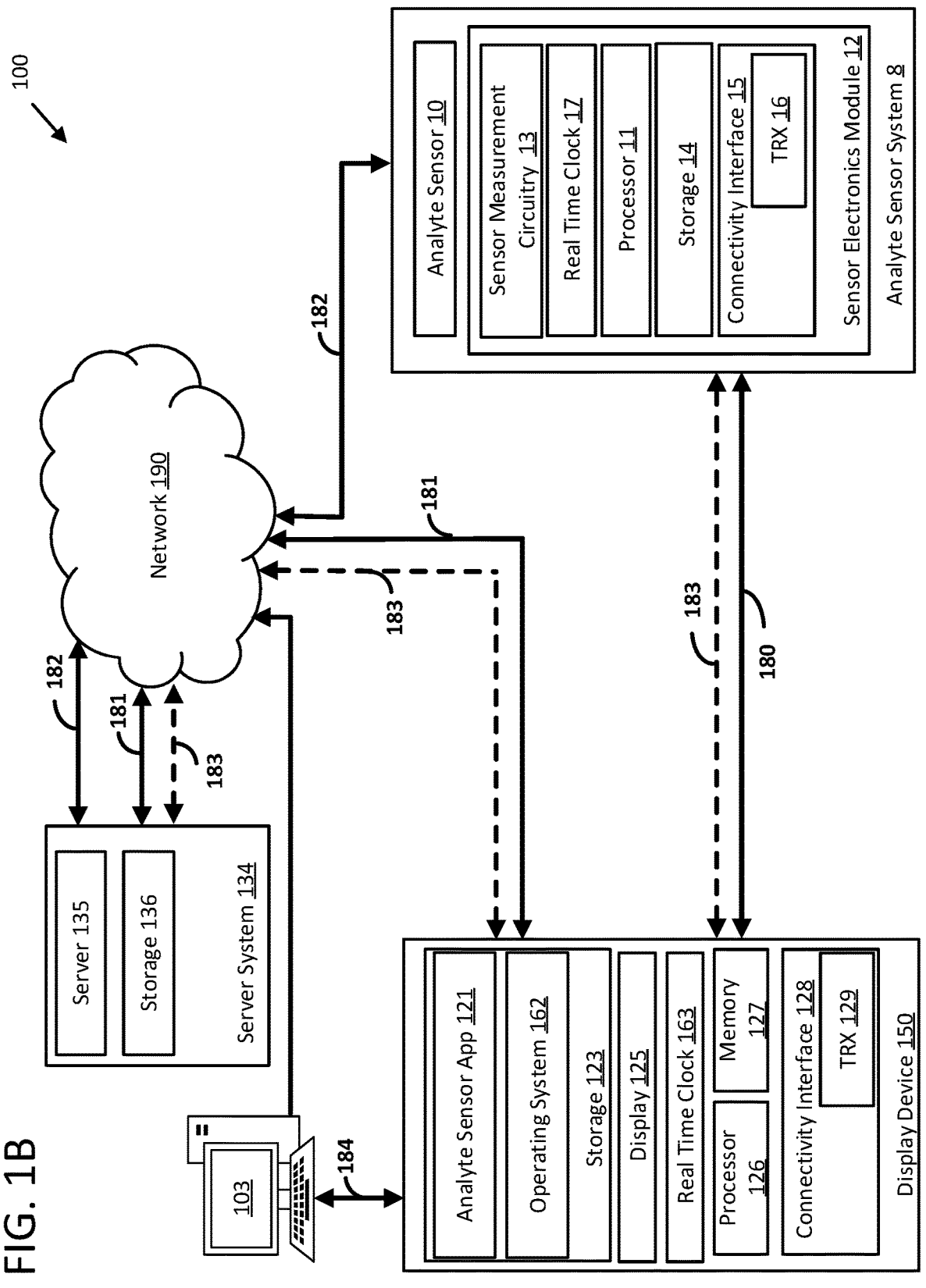
FIG. 1B illustrates the example diabetes management system of FIG. 1A in more detail, according to some embodiments disclosed herein.

FIG. 1B illustrates a more detailed view of system 100 including a display device 150 that is communicatively coupled to SS 8. In certain embodiments, display device 150 may be any one of display devices 110, 120, 130, and 140 of FIG. 1A. The communication path between SS 8 and display device 150 is shown as communication path 180. In certain embodiments, SS 8 and display device 150 are configured to wirelessly communicate over communication path 180 using a low-range wireless communication network (i.e., a communication network using one or more low range and/or distance wireless communication protocols). Examples of low range and/or distance wireless communication protocols include Bluetooth and Bluetooth Low Energy (BLE) protocols. In certain embodiments, other low range wireless communications may include Near Field Communications (NFC), radio frequency identification (RFID) communications, IR (infra red) communications, optical communications. In certain embodiments, wireless communication protocols other than low range and/or distance wireless communication protocols may be used for communication path 180, such as WiFi Direct. Display device 150 is also configured to connect to network 190 (e.g., local area network (LAN), wide area network (WAN), the Internet, etc.). For example, display device 150 may connect to network 190 via a wired (e.g., Ethernet) or wireless (e.g., WLAN, wireless WAN, cellular, Mesh network, personal area network (PAN) etc.) interface. Display device 150 is able to communicate with server system 134 through network 190. The communication path between display device 150 and server system 134 is shown as communication path 181 via network 190.

Note that, in certain embodiments, SS 8 may be able to independently (e.g., wirelessly) communicate with server system 134 through network 190. An independent communication path between SS 8 and server system 134 is shown as communication path 182. However, in certain other embodiments, SS 8 may not be configured with the necessary hardware/software to establish, for example, an independent wireless communication path with server system 134 through network 190. In such embodiments, SS 8 may communicate with server system 134 through display device 150. An indirect or pass-through communication path between SS 8 and server system 134 is shown as communication path 183.

System 100 additionally includes server system 134, which in turn includes server 135 that is coupled to storage 136 (e.g., one or more computer storage systems, cloud-based storage systems and/or services, etc.). In certain embodiments, server system 134 may be located or execute in a public or private cloud. In certain embodiments, server system 134 is located or executes on-premises ("on-prem"). As discussed, server system 134 is configured to receive, collect, and/or monitor information, including analyte data and related information, as well as encryption/authentication information from SS 8 and/or display device 150. Such information may include input responsive to the analyte data or input (e.g., the user's glucose measurements and other physiological/behavioral information) received in connection with an analyte monitoring or sensor application running on SS 8 or display device 150. This information may be stored in storage 136 and may be processed, such as by an analytics engine capable of performing analytics on the information. An example of an analyte sensor application that may be executable on display device 150 is analyte sensor application 121, as further described below.

In certain embodiments, server system 134 at least partially directs communications between SS 8 and display device 150, for example, for facilitating authentication therebetween. Such communications include messaging (e.g., advertisement, command, or other messaging), message delivery, and analyte data. For example, in certain embodiments, server system 134 may process and exchange messages between SS 8 and display device 150 related to frequency bands, timing of transmissions, security, alarms, and so on. In certain embodiments, server system 134 may also update information stored on SS 8 and/or display device 150. In certain embodiments, server system 134 may send/receive information to/from SS 8 and or display device 150 in real-time or sporadically. Further, in certain embodiments, server system 134 may implement cloud computing capabilities for SS 8 and/or display device 150.

Server system 134 may also be in communication with a web server (as part of a data management system) that provides access to patient data, including analyte data generated by SS 8 and transmitted to server system 134. For example, the web server may be accessed by patients and physicians by web browsers on various devices. Server system 134 may also be accessible by a software application that may be installed locally on a patient or a physician's device for accessing the patient's data.

FIG. 1B also illustrates the components of SS 8 in further detail. As shown, in certain embodiments, SS 8 includes analyte sensor 10 coupled to sensor electronics module 12. Sensor electronics module 12 includes sensor measurement circuitry 13 that is coupled to analyte sensor 10 for processing and managing sensor data. Sensor measurement circuitry 13 may also be coupled to processor 11. In some embodiments, processor 11 may perform part or all of the functions of the sensor measurement circuitry 13 for obtaining and processing sensor measurement values from analyte sensor 10. Processor 11 may also be coupled to storage 14 and real time clock (RTC) 17 for storing and tracking sensor data. In addition, processor 11 may be further coupled to a connectivity interface 15, which includes a radio unit or transceiver (TRX) 16 for sending sensor data and receiving requests and commands from an external device, such as display device 150. As used herein, the term transceiver generally refers to a device or a collection of devices that enable SS 8 to (e.g., wirelessly) transmit and receive data. SS 8 may further include storage 14 and real time clock (RTC) 17 for storing and tracking sensor data. It is contemplated that, in some embodiments, the senor measurement circuitry 13 may carry out all the functions of the processor 11 and vice versa.

Transceiver 16 may be configured with the necessary hardware and wireless communications protocols for enabling wireless communications between SS 8 and other devices, such as display device 150 and/or server system 134. For example, as described above, transceiver 16 may be configured with the necessary hardware and communication protocols to establish a Bluetooth or BLE connection with display device 150. As one of ordinary skill in the art appreciates, in such an example, the necessary hardware may include a Bluetooth or BLE security manager and/or other Bluetooth or BLE related hardware/software modules configured for Bluetooth or BLE communications standards. In some embodiments where SS 8 is configured to establish an independent communication path with server system 134, transceiver 16 may be configured with the necessary hardware and communication protocols (e.g., long range wireless cellular communication protocol, such as, GSM, CDMA, LTE, VoLTE, 3G, 4G, 5G communication protocols) for establishing a wireless connection to network 190 to connect with server system 134. As discussed elsewhere, other short range protocols, may also be used for communication between display device 150 and a SS 8 such as NFC, RFID, etc.

FIG. 1B similarly illustrates the components of display device 150 in further detail. As shown, display device 150 includes connectivity interface 128, processor 126, memory 127, a real time clock (RTC) 163, a display 125 for presenting a graphical user interface (GUI), and a storage 123.

A bus (not shown here) may be used to interconnect the various elements of display device 150 and transfer data between these elements. Connectivity interface 128 includes a transceiver (TRX) 129 used for receiving sensor data from SS 8 and for sending requests, instructions, and/or data to SS 8 as well as server system 134. Transceiver 129 is coupled to other elements of display device 150 via connectivity interface 128 and/or the bus. Transceiver 129 may include multiple transceiver modules operable on different wireless standards. For example, transceiver 129 may be configured with one or more communication protocols, such as wireless communication protocol(s) for establishing a wireless communication path with network 190 and/or low range wireless communication protocol(s) (e.g., Bluetooth or BLE) for establishing a wireless communication path 180 with SS 8. Additionally, connectivity interface 128 may in some cases include additional components for controlling radio and/or wired connections, such as baseband and/or Ethernet modems, audio/video codecs, and so on.

In some embodiments, when a standardized communication protocol is used between display device 150 and SS 8, commercially available transceiver circuits may be utilized that incorporate processing circuitry to handle low level data communication functions such as the management of data encoding, transmission frequencies, handshake protocols, security, and the like. In such embodiments, processor 126 of display device 150 and/or processor 11 of SS 8 may not need to manage these activities, but instead provide desired data values for transmission, and manage high level functions such as power up or down, set a rate at which messages are transmitted, and the like. Instructions and data values for performing these high level functions can be provided to the transceiver circuits via a data bus and transfer protocol established by the manufacturer of transceivers 129 and 16. However, in embodiments where a standardized communication protocol is not used between transceivers 129 and 16 (e.g., when non-standardized or modified protocols are used), processors 126 and 11 may be configured to execute instructions associated with proprietary communications protocols (e.g., one or more of the communications protocols described herein) to control and manage their respective transceivers. In addition, when non-standardized or modified protocols are used, customized circuitries may be used to service such protocols.

Processor 126 may include processor sub-modules, including, by way of example, an applications processor that interfaces with and/or controls other elements of display device 150 (e.g., connectivity interface 128, analyte sensor application 121 (hereinafter "sensor application 121"), display 125, RTC 163, memory 127, storage 123, etc.). In certain embodiments, processor 126 is configured to perform functions related to device management, such as, for example, managing lists of available or previously paired devices, information related to network conditions (e.g., link quality and the like), information related to the timing, type, and/or structure of messaging exchanged between SS 8 and display device 150, and so on. Processor 126 may further be configured to receive and process user input, such as, for example, a user's biometric information, such as the user's finger print (e.g., to authorize the user's access to data or to be used for authorization/encryption of data, including analyte data), as well as analyte data.

Processor 126 may include and/or be coupled to circuitry such as logic circuits, memory, a battery and power circuitry, and other circuitry drivers for periphery components and audio components. Processor 126 and any sub-processors thereof may include logic circuits for receiving, processing, and/or storing data received and/or input to display device 150, and data to be transmitted or delivered by display device 150. As described above, processor 126 may be coupled by a bus to display 125, connectivity interface 128, storage 123, etc. Hence, processor 126 may receive and process electrical signals generated by these respective elements and thus perform various functions. By way of example, processor 126 may access stored content from storage 123 and memory 127 at the direction of analyte sensor application 121, and process the stored content to be displayed by display 125. Additionally, processor 126 may process the stored content for transmission via connectivity interface 128 to SS 8 and/or server system 134. Display device 150 may include other peripheral components not shown in detail in FIG. 1B.

In certain embodiments, memory 127 may include volatile memory, such as random access memory (RAM) for storing data and/or instructions for software programs and applications, such as analyte sensor application 121. Display 125 presents a GUI associated with operating system 162 and/or analyte sensor application 121. In various embodiments, a user may interact with analyte sensor application 121 via a corresponding GUI presented on display 125. By way of example, display 125 may be a touchscreen display that accepts touch input. Analyte sensor application 121 may process and/or present analyte-related data received by display device 150 and present such data via display 125. Additionally, analyte sensor application 121 may be used to obtain, access, display, control, and/or interface with analyte data and related messaging and processes associated with SS 8 (e.g., and/or any other medical device (e.g., insulin pump or pen) that are communicatively coupled with display device 150), as is described in further detail herein.

Storage 123 may be a non-volatile storage for storing software programs, instructions, data, etc. For example, storage 123 may store analyte sensor application 121 that, when executed using processor 126, for example, receives input (e.g., by a conventional hard/soft key or a touch screen, voice detection, or other input mechanism), and allows a user to interact with the analyte data and related content via display 125. In various embodiments, storage 123 may also store user input data and/or other data collected by display device 150 (e.g., input from other users gathered via analyte sensor application 121). Storage 123 may further be used to store volumes of analyte data received from SS 8 (or any other medical data received from other medical devices (e.g., insulin pump, pen, etc.) for later retrieval and use, e.g., for determining trends and triggering alerts.

As described above, SS 8, in certain embodiments, gathers analyte data from analyte sensor 10 and transmits the same or a modified version of the collected data to display device 150. Data points regarding analyte values may be gathered and transmitted over the life of analyte sensor 10 (e.g., in the range of 1 to 30 days or more). New measurements may be transmitted often enough to adequately monitor glucose levels. In certain embodiments, rather than having the transmission and receiving circuitry of each of SS 8 and display device 150 continuously communicate, SS 8 and display device 150 may regularly and/or periodically establish a communication channel among each other. Thus, in such embodiments, SS 8 may, for example, communicate with display device 150 at predetermined time intervals. The duration of the predetermined time interval can be selected to be long enough so that SS 8 does not consume too much power by transmitting data more frequently than needed, yet frequent enough to provide substantially real-time sensor information (e.g., measured glucose values or analyte data)

to display device 150 for output (e.g., via display 125) to the user. While the predetermined time interval is every five minutes in some embodiments, it is appreciated that this time interval can be varied to be any desired length of time. In other embodiments, transceivers 129 and 16 may be continuously communicating. For example, in certain embodiments, transceivers 129 and 16 may establish a session or connection there between and continue to communicate together until the connection is lost.

Analyte sensor application 121 may be downloaded, installed, and initially configured/setup on display device 150. For example, display device 150 may obtain analyte sensor application 121 from server system 134, or from another source, such as an application store or the like, via a network, e.g., network 190. Following installation and setup, analyte sensor application 121 may be configured to access, process, and/or interface with analyte data (e.g., whether stored on server system 134, locally from storage 123, from SS 8, or any other medical device). By way of example, analyte sensor application 121 may present a menu that includes various controls or commands that may be executed in connection with the operation of SS 8, display device 150, one or more other display devices (e.g., display device 110, 130, 140, etc.), and/or one or more other partner devices, such as an insulin pump. For example, analyte sensor application 121 may be used to interface with or control other display and/or partner devices, for example, to deliver or make available thereto analyte data, including for example by receiving/sending analyte data directly to the other display and/or partner device and/or by sending an instruction for SS 8 and the other display and/or partner device to be connected.

As discussed above, certain embodiments herein include proximity-based authentication and authorization techniques for providing access to patient data. The use of proximity in data access, authentication, and/or authorization in a data management system that controls access to medical data can be illustrated with a few example use-cases. A first use-case may involve a patient who wishes to obtain access to the patient's own data using a device. A second use-case may involve a physician at a clinic who wishes to obtain access to data of a patient who is present at the clinic.

In the first example use-case, a patient who uses SS 8 to monitor their analyte data may wish to view her long-term medical data including previously generated analyte data using SS 8. For example, SS 8 may have been continuously used by the patient to generate analyte data that was periodically transmitted (e.g., through display device 150) to server system 134 and, for example, stored in storage 136.

The patient may then reach for a display device (hereinafter "DD") (e.g., display device 150, which may be any one of display devices 120, 130, or a laptop or any other computing system with low or short range communication capabilities and an operating system able to execute a web browser) and proceed to use a browser to bring up a website associated with a data management system that controls access to data that is stored at server system 134. Note that in the embodiments described herein DD may be different or the same as the display device that is in constant communication with SS 8 to continuously receive the patient's analyte measurements.

Continuing with the example above, the patient brings up the website in order to access their analyte data (and/or data reports), which may have been generated previously with SS 8 or a different sensor system (a previous SS). The data management system may be an on-premise or a cloud-based server or system and may include a web server that is configured to provide access to the data that is stored at server system 134 in response to web requests through a browser executing on DD. The DD may have its Bluetooth, Bluetooth Low Energy (BLE) (or any other low range communication component) communication module and antenna on, and it may scan for advertisements from SS 8.

When the patient attempts to access the website to view her data, the browser may be configured to insert SS-identifiable data into a web request (e.g., the HTTP/HTTPS GET request) that is generated by the web browser. The SS-identifiable data identified SS 8 and will indicate to the data management system that the person who is requesting access to the data is in close proximity of SS 8 and, therefore, should be trusted. Different types of SS-identifiable data that can be verified by the web server (or other components or the data management system) as being associated with the patient's SS 8 are discussed in more detail below. Once the web server verifies that the SS-identifiable data belongs to the SS associated with a patient whose data is being requested, the web server could then grant access to the data request and perform a login. This login could be accomplished without a password or could be done with a password to achieve multifactor authentication.

One of a variety of techniques may be used to configure a web browser to insert SS identifiable information in a web request. For example, a software application that is locally installed on the DD may be configured to receive the SS advertisements and communicate with the web browser to insert SS identifiable information in a web request. In another example, the web browser may be configured to communicate with an API provided by the low range communications stack at the DD. For example, the web browser may be configured to communicate with a BLE API provided by the BLE stack at the DD. In such examples, the web browser may directly receive the SS identifiable information from DD's BLE stack. In certain embodiments, the web browser may be configured to use the BLE API to continuously communicate with the BLE stack and scan for any BLE advertisements that may be received by the BLE stack.

Using data advertised by SS 8 as a way to authenticate the patient is advantageous because generally an attacker cannot access or intercept the data that is in SS 8's advertisements. As long as an attacker is not within a range where they can see (e.g., intercept, listen to, etc.) the patient's SS 8's advertisements, then the patient's access to their data can be considered a form of data access that is secure.

In this model, multiple techniques may be used to further increase the probability that an attacker would not be able to obtain access to the patient's data. For example, if an attacker is within proximity and just listens to the patient's SS 8, the attacker would gain read access to the patient's data through the website. As such, one technique to reduce the attacker's ability to access the patient's data is to require a patient's username (not a secret but still requires one to guess a correct value) on the website. Further, the number of times usernames can be tried on the website for a specific patient can be throttled.

The assumption that an attacker cannot access a patient's data stream when the attacker is not in proximity of the patient's sensor system, is based on another assumption that the attacker is not able to guess or brute force the SS identifiable data, in SS 8's advertisements when the attacker is not within allowable proximity. Accordingly, certain embodiments described herein propose multiple ways for enforcing or using SS identifiable information that an attacker would not be able to brute force including.

For example, in certain embodiments, the identifiable SS information may include the last N number of analyte values (e.g., blood glucose values), where N is a positive integer value. The web server is able to verify the last N number of glucose values for the patient because the web server has access to the patient's analyte data (e.g., stored in storage 136), which is up-to-date and includes the last N number of glucose values. Note that the patient's analyte data is generated and provided by SS 8 and transmitted to server system 134 (e.g., directly or through analyte sensor app 121 on display device 150) which either includes or is in communication with the data management system, including the web server. If the web server is able to determine that the last N glucose values in the patient's data is the same as the last N glucose values in the SS 8 advertisement that was received as part of the web request, then the web server allows access to the patient data.

In another example, the identifiable SS information may include the last N number of RSSI values. For example, analyte sensor app 121 executing on display device 150 may have received the last 5 consecutive signals with 5 RSSI values and transmit those values to the server system 134 as part of the patient data. In such an example, if the web server is able to determine that the last N RSSI values in the patient's data is the same as the last N RSSI values in the SS 8 advertisement that was received as part of the web request, then the web server allows access to the patient data.

In another example, the identifiable SS information may include a secret value that cannot be easily brute forced. For example, the secret value could be a 128-bit or 256-bit random secret. This secret value could similarly be stored as part of the patient's data in server system 134 and may be used by the web server to compare against the secret value in the SS 8 advertisement that was received as part of the web request.

In certain embodiments, the identifiable SS information may include BLE chip specific information associated with SS 8. The BLE chip specific information may be received by the server system 134 as part of, for example, the patient data during the pairing process between SS 8 and display device 150. The web server may the BLE chip specific information that is stored as part of the patient data against the BLE chip specific information in the SS 8 advertisement that was received as part of the web request.

In certain embodiments, the identifiable information may relate to analyte sensor application 121 executing on display device 150 that the patient uses to continuously monitor their analyte measurements. For example, the identifiable information may include a unique app ID, a signed app value, etc. The app-related identifiable information may be stored as part of the patient's data in server system 134 and may be used by the web server to compare against the identifiable information in the SS 8 advertisement that was received as part of the web request.

In certain embodiments, the identifiable information may relate to the specific display device 150 that the patient uses to continuously monitor their analyte measurements. The display device related identifiable information may be stored as part of the patient's data in server system 134 and may be used by the web server to compare against the identifiable information in the SS 8 advertisement that was received as part of the web request.

In certain embodiments, to ensure that the data in the sensor system advertisements does not give one access to a patient data set for all time, the identifiable information may be configured to expire. As such, in certain embodiments, the identifiable information is configured to change over time. This could be achieved in a number of ways. For example, using the last N number of glucose values, or the last N number of RSSI values as identifiable information ensures that the identifiable information periodically changes.

For identifiable information that may not be guaranteed to change (e.g., a 128-bit or 256-bit random secret), SS 8 may be configured to perform some function like: identifiable information=function (dynamic value, master_secret). In certain embodiments, the function is a cryptographic hash function such as SHA3 or AES. The identifiable information is sufficiently long and will change over time, and the data management system can determine if the computed identifiable information is valid, as long as the data management system has access to the master_secret and the function used to calculate the identifiable information.

As an example, SS 8 may compute: identifiable information=AES (nonce_counter, tx_master_key). The DD (e.g., laptop) attempting to access the patient's data will transmit the identifiable information as part of the web request to the web server. The data management system, which has access to the tx_master_key is able to compute the identifiable information, because it is in possession of the tx_master_key. Therefore, the data management system is able to compare the tx_master_key it is in possession of with the tx_master_key in the AES and grant access to the patient's data if they are the same.

In certain embodiments, the identifiable information may expire after a certain amount of time that may be configurable (e.g., T=30 minutes). Once the identifiable information expires, the DD will need to get a new identifiable information from SS 8. SS 8 may, for example, compute new identifiable information every T (e.g., 30) minutes. As an example, new identifiable information could be computed in the form of: identifiable information=AES (nonce_counter+1, tx_master_key).

In certain embodiments, the wireless communication range may be reduced intentionally (by reducing the transmission power) to reduce the likelihood of attacks. No matter the distance or radio protocol that is used, the probability that an attacker can receive data from a transmitted signal can be reduced by having the SS 8 to use less transmission power. By using less power, the attacker would have to be much closer to SS 8 to receive the advertisement and 2) use better equipment to hear a signal from SS 8.

In certain embodiments, the number of data points that are required for authentication to access the patient's information may be increased for additional security. Accordingly, any two or more methods or types of identifiable information may be used as a combination for authentication.

As discussed above, a second use-case where proximity may be used in data access, authentication, and/or authorization may involve a physician at a clinic who wishes to obtain access to data of a patient who is present at the clinic. In such an example, the patient, who is wearing SS 8 and is also in possession of their display device 150, is scheduled to be seen by the physician. In some cases, one way to provide the physician with access to the patient's data may involve having the physician request the patient's data by clicking on a link and, in response, asking the patient the patient to use analyte sensor app 121 to generate and display a unique code, e.g., QR code. The physician could use their DD to copy the QR code data and use that data as an authentication token. However, this approach requires multiple actions and interactions to be performed by the physician and the patient in order for the physician to gain access to the data.

Accordingly, in certain embodiments, the physician may use a DD (e.g., a laptop, iPad, iPhone, or any other mobile device at the clinic that is configured with wireless communications capabilities, such as Bluetooth or BLE capabilities) to access a website in order to access the patient's data. The website may be associated with the data management system or in communication with a web server that is in communication with the data management system. Similar to the first use-case, in the second user-case, the physician's DD may be enabled to scan for and/or receive advertisements transmitted by the patient's SS 8 and insert the identifiable information in the advertisements into a HTTP/HTTPS GET request that is generated by the web browser to access the website. The identifiable information will indicate to the data management system that the person who is requesting access to the data is in close proximity of SS 8 and, therefore, should be trusted. Different types of SS-identifiable data that can be verified by the web server (or other components or the data management system) as being associated with the patient's SS 8 were discussed above.

One of a variety of techniques may be used to configure a web browser to insert SS identifiable information in a web request. For example, a software application that is locally installed on the physician's DD may be configured to scan for and/or receive the SS advertisements and communicate with the web browser to insert SS identifiable information in a web request. In another example, the web browser may be configured to communicate with an API provided by the low range communications stack at the DD. For example, the web browser may be configured to communicate with a BLE API provided by the BLE stack at the DD. In such examples, the web browser may directly receive the SS identifiable information from DD's BLE stack. In certain embodiments, the web browser may be configured to use the BLE API to continuously communicate with the BLE stack and scan for any BLE advertisements that may be received by the BLE stack.

In certain embodiments, the web browser may be configured to determine when a certain patient's visit is and, automatically, send a web request to the web server with the identifiable information received from the patient's SS 8 as well as a list of patient names scheduled to visit that dat. For example, the physician's DD may run a software or have access to a website or a system that has the list of names and other information associated with of all the patients who are scheduled for visits during a certain day as well as the times of the visit. As such, once a patient's scheduled visit is close, the physician's DD may continuously or periodically scan for identifiable information associated with that patient. When the SS of the patient sends advertisements to the physician's DD, the DD inserts the identifiable information in a web request as well as some secondary information about the patient (e.g., public information, such as name, address, etc.). At the other end, the web server checks the patient data associated with the patient (based on the patient name) to see if the identifiable data received in the web request matches any the identifiable date in the patient data. If there is a match, the web server provides access to the patient's data. In such an example, no interaction is required either by the physician or the patient.

In certain embodiments, there might be two or more patients at the clinic at the same time, in which case the physician's DD may transmit a request to the display device 150 of the patient whose scheduled visit is next in order for the display device 150 to play an audible sound (e.g., a specific audible sound). The physician's DD may then have a microphone to determine the received specific audible. If there is a match, then the physician's DD can determine and confirm that the advertisement that is being received from an SS belongs to the patient whose schedule visit is next. In another example, the physician's DD may transmit a request to the display device 150 of the patient whose scheduled visit is next in order for the display device 150 to transmit the last N number of RSSI values to server system 134. In that example, the SS identifiable information received in the advertisement received from the patient's SS 8 may include the same N number of RSSI value. The web server is then able to compare the RSSI values in the patient data and the RSSI values received in the SS 8 advertisements and grant the physician access to the data if they match.

In certain embodiments, in the second use-case, the physician's or a follower's DD may transmit a BLE message that could be picked up by display device 150 (e.g., by analyte sensor app 121 running on display device 150). The message may be a request to allow the DD to access the patient's data for N months (e.g., 24 months). On display device 150 the patient may then see a pop-up window to ask the patient for permission to allow DD to access the patient's data. Once the patient approves, display device 150 transmits a secret token value that will enable display device 150 to retrieve patient data for the next N=24 months. At the end of those 24 months, the token will timeout.

In another embodiment, a patient could change the length of period of time for a token's validity, but this increases complexity for fine-grained access control. In another embodiment, the person controlling the laptop for access (e.g., patient or physician) could configure the request to allow for N=12 months or N=60 months.

Figure 2:
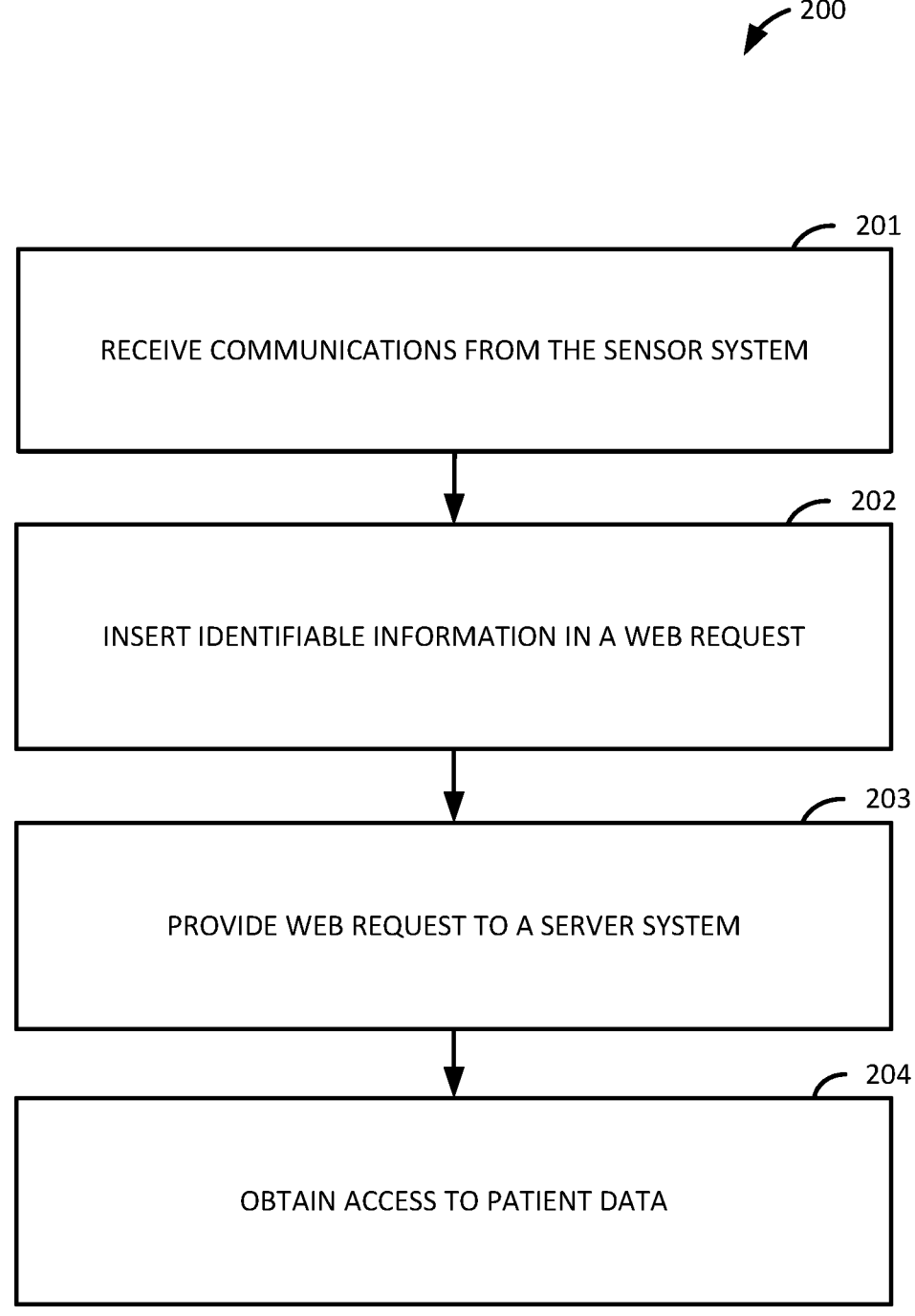
FIG. 2 is a flowchart diagram of an example process for securely obtaining access to patient data associated with a patient that is collected by a sensor system for monitoring analyte levels of the patient, according to some embodiments disclosed herein.

FIG. 2 is a flow diagram of an example process 200 for a DD (e.g., the DD 150 of FIG. 1B) to obtain access to patient data stored by a server system (e.g., the server system 134 of FIG. 1B) using proximity-based authentication techniques. As described above, the patient data stored by the server system may have been collected by and received from an SS (e.g., the SS 8 of FIGS. 1A-1B) to monitor analyte levels of a patient.

As depicted in FIG. 2, the process 200 begins at block 201 when the DD receives one or more communications from the SS. In some embodiments, the SS transmits the one or more communications via a low or short range wireless communication network. As described above, a low range wireless communication network may use one or more low/short range wireless communication protocols, such as at least one of Bluetooth, BLE, RFID, or NFC. In some embodiments, the low range wireless communication network is configured such that only devices that are within a threshold proximity of the SS can receive communications that are transmitted by the SS and using the low range wireless communication network.

In some embodiments, the low range wireless communication network is associated with a communication protocol, and the communication protocol defines a set of data channels and a set of communication channels. A data channel is a communication channel that can be used to transmit data between a sender device to a destination device (e.g., from the SS to the DD) after establishing a connection between the two devices. An advertisement communication channel is a communication channel that can be used to broadcast data from a sender device (e.g., from the SS) without establishing connection with the recipient devices (e.g., with the DD). In some embodiments, the frequencies of advertisement channels are selected to minimize radio interferences (e.g., interferences from nearby Wi-Fi activity) on these channels. For example, BLE uses three communication channels having a 2402 MHz, a 2426 MHz, and a 2480 MHz frequency respectively. The BLE additionally uses 37 data channels.

In some embodiments, the SS transmits the communications using an advertisement channel of the communication protocol associated with the low or short range wireless communication network. Transmitting the communications using the advertisement channel is advantageous because advertisement channels do not require a full connection between the SS and any recipient devices (e.g., the DD) and thus minimize network connection overhead for both the SS and the recipient devices. Moreover, because the frequencies of advertisement channels may be selected to minimize radio interference such as Wi-Fi activity on these channels, using advertisement channels can minimize the effect of the advertisement channel communications on WiFi-enabled communications of the SS (e.g., Wi-Fi enabled communications between the SS and the server system or other nearby Wi-Fi communications).

At block 202, the DD inserts identifiable information determined based on the one or more communications in a web request. In some embodiments, the identifiable information include authentication tokens that are described in the one or more communications. In some embodiments, the DD determines the identifiable information based on computed features of the one or more communications.

In some embodiments, the SS is a continuous analyte sensor system that is configured to transmit one or more analyte values of a host via advertisement channel communications. In such embodiments, the identifiable information may comprise a defined number of (i.e., N) the latest analyte values transmitted by the continuous analyte sensor system. In some of the noted embodiments, each communication transmitted from the SS via an advertisement channel describes a latest analyte value of the host, and the identifiable information is determined based on the analyte values described in latest N advertisement channel communications. Accordingly, in some embodiments, to determine identifiable information based on the advertisement channel communications, the DD: (i) collects the latest N advertisement channel communications from SS, (ii) extracts analyte values reported by the collected communications, and (iii) determines the identifiable information based on the extracted analyte values. In some embodiments, in addition to transmitting analyte values of the host using advertisement channel communications, the SS also transmits the analyte values to the server system via a secure connection.

As another example, in some embodiments, the sensor system is a continuous sensor system that is configured to continuously transmit communications to the display device, and the one or more communications comprise a defined number of (N) latest communications transmitted by the continuous sensor system. In some of the noted embodiments, the identifiable information comprises RSSI values for the defined number of latest communications. Accordingly, in some embodiments, to determine the identifiable information, the SS: (i) collects the latest N advertisement channel communications from SS, (ii) determines RSSI values for the collected communications, and (iii) determines the identifiable information based on the determined RSSI values. In some embodiments, the SS also transmits the received signal strength indicator values for advertisement channel communications to the server system via a secure connection.

In some embodiments, the SS is configured to transmit the communication using a BLE chip, and the identifiable information comprises chip identifier data associated with the BLE chip. In some embodiments, the chip identifier of the BLE chip of the SS is described in the one or more communications transmitted by the SS using an advertisement channel. In some embodiments, the SS also transmits the chip identifier for the BLE chip to the server system via a secure connection.

At block 203, the DD provides the web request including the identifiable information to the server system to request access to patient data. At block 204, the DD obtains access to the patient if the server system authenticates the DD based on the information in the web request.

In some embodiments, the web request comprises, in addition to the identifiable information, one or more user authentication token fields that are maintained by the display device. In some embodiments, the web server enables the DD to access the patient data after the web server verifies that: (i) the identifiable information in the web request match identifiable information maintained by the web server, and (ii) the one or more user authentication token fields in the web request match one or more user authentication token fields maintained by the server system.

Note that in addition to the various advantages of the proximity-based authentication techniques described herein, the proximity-based authentication techniques described herein more efficiently utilize computer network resources for transmitting identifiable information used for authentication. For example, as further described below, some embodiments involve performing authentication based on communications that are transmitted as part of normal operations of a system and for reasons other than authentication (e.g., sensor output communications). In such examples, transmitting such communications is sufficient to enable a receiving device to perform authentication. Thus, in such embodiments, there is no need to transmit any additional identifiable information using new packets/messages beyond the packets/messages used for communications transmitted as part of normal operations of the system. Accordingly, some embodiments reduce the overall number of packets/messages transmitted over the network that is associated with the system.

Figure 3:
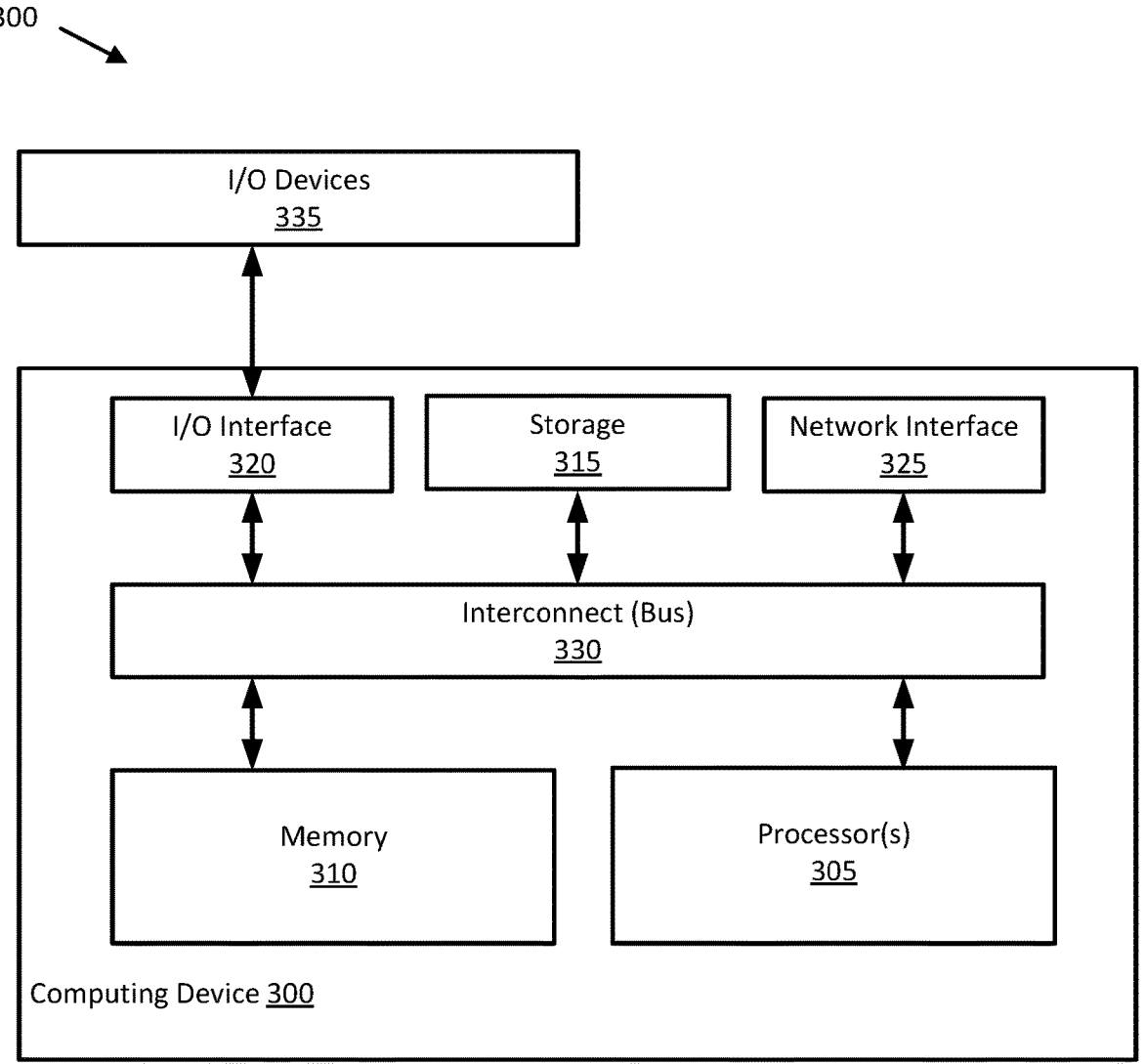
FIG. 3 is a block diagram depicting an example computing device configured to authorize access to patient data associated with a patient, according to certain embodiments disclosed herein.

FIG. 3 is a block diagram depicting an example computing device 300 configured to authorize access to patient data associated with a patient, according to certain embodiments disclosed herein. Although depicted as a single physical device, in embodiments, computing device 300 may be implemented using virtual device(s), and/or across a number of devices, such as in a cloud environment. As illustrated, computing device 300 includes a processor 305, memory 310, storage 315, a network interface 325, and one or more input/output (I/O) interfaces 320. In the illustrated embodiment, processor 305 retrieves and executes programming instructions stored in memory 310, as well as stores and retrieves data residing in storage 315. In certain embodiments, memory 310 is configured to store instructions (e.g., computer-executable code) that when executed by processor 305, cause processor 305 to perform the operations of a data management system.

Processor 305 is generally representative of a single central processing unit (CPU) and/or graphics processing unit (GPU), multiple CPUs and/or GPUs, a single CPU and/or GPU having multiple processing cores, and the like. Memory 310 is generally included to be representative of a random access memory (RAM). Storage 315 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 335 (such as keyboards, monitors, etc.) can be connected via the I/O interface(s) 320. Further, via network interface 325, computing device 300 can be communicatively coupled with one or more other devices and components. In certain embodiments, computing device 300 is communicatively coupled with other devices via a network, which may include the Internet, local network(s), and the like. The network may include wired connections, wireless connections, or a combination of wired and wireless connections. As illustrated, processor 305, memory 310, storage 315, network interface(s) 325, and I/O interface(s) 320 are communicatively coupled by one or more interconnects 330. In certain embodiments, computing device 300 is a server executing in an on-premises data center or a cloud environment.

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, acc, b-b, b-b-b, b-b-c, c-c, and c-c-c or any other ordering of a, b, and c).

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U. S. C. § 112(f) unless the element is expressly recited using the phrase "means for" or, in the case of a method claim, the element is recited using the phrase "step for."

While various examples of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various example examples and aspects, it should be understood that the various features and functionality described in one or more of the individual examples are not limited in their applicability to the particular example with which they are described. They instead can be applied, alone or in some combination, to one or more of the other examples of the disclosure, whether or not such examples are described, and whether or not such features are presented as being a part of a described example. Thus the breadth and scope of the present disclosure should not be limited by any of the above-described example examples.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide example instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular example of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

The term "comprising as used herein is synonymous with "including," "containing," or "characterized by" and is inclusive or open-ended and does not exclude additional, unrecited elements or method steps.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific examples and examples described herein, but rather to also cover all modification and alternatives coming with the true scope and spirit of the invention.

The invention claimed is:

1. A method of securely obtaining access to patient data associated with a patient using a sensor system for monitoring analyte levels of the patient, comprising:

receiving, by a display device, one or more communications from the sensor system, wherein the sensor system is a continuous analyte sensor system, wherein the one or more communications:

include identifiable information of a host of the sensor system, the identifiable information comprising a defined number of latest analyte values reported by the continuous analyte sensor system, and are transmitted by the sensor system via an advertisement channel;

inserting, by the display device, the identifiable information of the sensor system in a web request;

providing, by the display device, the web request including the identifiable information of the host to a data management system to request access to the patient data; and obtaining access to the patient data through a web browser upon the data management system verifying that the identifiable information of the host matches a second identifiable information of the host stored in the patient data.

2. The method of claim 1, wherein:

the sensor system is a continuous sensor system that is configured to continuously transmit communications to the display device, the one or more communications comprise a defined number of latest communications transmitted by the continuous sensor system, and the identifiable information of the host comprises received signal strength indicator values for the defined number of latest communications.

3. The method of claim 1, wherein the one or more communications are transmitted via a low or a short range wireless communication network.

4. The method of claim 3, wherein:
the sensor system is configured to communicate via the low range wireless communication network using a Bluetooth Low Energy (BLE) chip, and
the identifiable information of the host comprises chip identifier data associated with the BLE chip.

5. The method of claim 3, wherein:
the low range wireless communication network is associated with a communication protocol, and
the communication protocol is associated with a set of data channels and a set of advertisement channels comprising the advertisement channel that is used to transmit the one or more communications.

6. The method of claim 1, wherein:
the web request comprises one or more authentication token fields that are maintained by the display device, and
access to the patient data through the web browser is obtained upon the data management system verifying that the identifiable information of the host matches the second identifiable information of the host stored in the patient data and the one or more authentication token fields match one or more second authentication token fields maintained by the data management system.

7. A method of authorizing access to patient data associated with a patient using a sensor system for monitoring analyte levels of the patient, comprising:
receiving, by a data management system, a web request from a display device, the web request indicating a request for access to the patient data and including identifiable information of a host of the sensor system, wherein the sensor system is a continuous analyte sensor system, wherein the identifiable information of the host is provided by one or more communications that are transmitted to the display device from the sensor system via an advertisement channel, the identifiable information comprising a defined number of latest analyte values reported by the continuous analyte sensor system;
verifying, by the data management system, that the identifiable information of the host matches a second identifiable information of the host stored in the patient data; and
granting, by the data management system, the request for access to the patient data based on the verifying.

8. The method of claim 7, wherein:
the sensor system is a continuous sensor system that is configured to continuously transmit communications to the display device,
the one or more communications comprise a defined number of latest communications transmitted by the continuous sensor system, and
the identifiable information of the host comprises received signal strength indicator values for the defined number of latest communications.

9. The method of claim 7, wherein the one or more communications are transmitted via a low or a short range wireless communication network.

10. The method of claim 9, wherein:
the sensor system is configured to communicate via the low range wireless communication network using a Bluetooth Low Energy (BLE) chip, and
the identifiable information of the host comprises chip identifier data associated with the BLE chip.

11. The method of claim 9, wherein:
the low range wireless communication network is associated with a communication protocol, and
the communication protocol is associated with a set of data channels and a set of advertisement channels comprising the advertisement channel that is used to transmit the one or more communications.

12. The method of claim 7, wherein:
the web request comprises one or more authentication token fields that are maintained by the display device, and
access to the patient data is obtained upon the data management system verifying that the identifiable information of the host matches the second identifiable information of the host stored in the patient data and the one or more authentication token fields match one or more second authentication token fields maintained by the data management system.

13. A system for securely obtaining access to patient data associated with a patient using a sensor system for monitoring analyte levels of the patient, the system comprising a memory comprising executable instructions and a processor in data communication with the memory and configured to execute the instructions to cause the system to perform operations of a method comprising:
receiving, by a display device, one or more communications from the sensor system, wherein the sensor system is a continuous analyte sensor system, wherein the one or more communications:
include identifiable information of a host of the sensor system, the identifiable information comprising a defined number of latest analyte values reported by the continuous analyte sensor system, and
are transmitted by the sensor system via an advertisement channel;
inserting, by the display device, the identifiable information of the host in a web request;
providing, by the display device, the web request including the identifiable information of the host to a data management system to request access to the patient data; and
obtaining access to the patient data through a web browser upon the data management system verifying that the identifiable information of the host matches a second identifiable information of the host stored in the patient data.

14. The system of claim 13, wherein:
the sensor system is a continuous sensor system that is configured to continuously transmit communications to the display device,
the one or more communications comprise a defined number of latest communications transmitted by the continuous sensor system, and
the identifiable information of the host comprises received signal strength indicator values for the defined number of latest communications.

15. The system of claim 13, wherein the one or more communications are transmitted via a low range wireless communication network.

16. The system of claim 15, wherein:

the sensor system is configured to communicate via the low range wireless communication network using a Bluetooth Low Energy (BLE) chip, and the identifiable information of the host comprises chip identifier data associated with the BLE chip.

17. The system of claim 15, wherein:

the low range wireless communication network is associated with a communication protocol, and the communication protocol is associated with a set of data channels and a set of advertisement channels comprising the advertisement channel that is used to transmit the one or more communications.

\* \* \* \* \*